US00PP31041P2

(12) United States Plant Patent
Norton

(10) Patent No.: US PP31,041 P2
(45) Date of Patent: Nov. 12, 2019

(54) ***ABELIA* PLANT NAMED 'RNTOM'**

(50) Latin Name: ***Abelia* x *grandiflora***
Varietal Denomination: RNTOM

(71) Applicant: Randall Jerry Norton, Alto, GA (US)

(72) Inventor: Randall Jerry Norton, Alto, GA (US)

( * ) Notice: Subject to any disclaimer, the term of this patent is extended or adjusted under 35 U.S.C. 154(b) by 0 days.

(21) Appl. No.: 15/998,210

(22) Filed: Jul. 13, 2018

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ... A01H 5/02; A01H 5/00; A01H 5/12; A01H 6/00
See application file for complete search history.

(56) References Cited

U.S. PATENT DOCUMENTS

PP30,430 P2 * 4/2019 Pineau ..... A01H 5/00 Plt./226

* cited by examiner

*Primary Examiner* — June Hwu
(74) *Attorney, Agent, or Firm* — C. A. Whealy

(57) ABSTRACT

A new and distinct cultivar of *Abelia* plant named 'RNTOM', characterized by its compact, uniformly upright to somewhat outwardly spreading and rounded plant habit; relatively slow in plant growth and require less frequent pruning in the landscape; freely branching habit; dense and bushy growth habit; leaves that are medium to small in size; under full sunlight conditions, developing foliage is yellow orange in color becoming bright yellow green with development; white-colored flowers; and good garden performance.

2 Drawing Sheets

Botanical designation: *Abelia* x *grandiflora*.
Cultivar denomination: 'RNTOM'.

BACKGROUND OF THE INVENTION

The present invention relates to a new and distinct cultivar of *Abelia* plant, botanically known as *Abelia* x *grandiflora* and hereinafter referred to by the name 'RNTOM'.

The new *Abelia* plant is a naturally-occurring branch mutation of *Abelia* x *grandiflora* 'Canyon Creek', not patented. The new *Abelia* plant was discovered and selected by the Inventor in August, 2013 on a single plant within a population of plants of 'Canyon Creek' in a controlled outdoor nursery environment in Alto, Ga.

Asexual reproduction of the new *Abelia* plant by semi-hardwood and hardwood cuttings in a controlled greenhouse environment in Alto, Ga. since June, 2014 has shown that the unique features of this new *Abelia* plant are stable and reproduced true to type in successive generations of asexual reproduction.

SUMMARY OF THE INVENTION

Plants of the new *Abelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'RNTOM'. These characteristics in combination distinguish 'RNTOM' as a new and distinct *Abelia* plant:

1. Compact, uniformly upright to somewhat outwardly spreading and rounded plant habit.
2. Relatively slow in plant growth and require less frequent pruning in the landscape.
3. Freely branching habit; dense and bushy growth habit.
4. Leaves that are medium to small in size.
5. Under full sunlight conditions, developing foliage is yellow orange in color becoming bright yellow green with development.
6. White-colored flowers.
7. Good garden performance.

Plants of the new *Abelia* can be compared to plants of the mutation parent, 'Canyon Creek'. In side-by-side comparisons, plants of the new *Abelia* differ primarily from plants of 'Canyon Creek' in the following characteristics:

1. Plants of the new *Abelia* are more compact than plants of 'Canyon Creek'.
2. Plants of the new *Abelia* are slower-growing than plants of 'Canyon Creek'.
3. Under full sunlight conditions, fully developed leaves of plants of the new *Abelia* are bright yellow green in color whereas fully developed leaves of plants of 'Canyon Creek' are golden yellow and green in color.

Plants of the new *Abelia* can be compared to plants of *Abelia* x *grandiflora* 'Minacara1', disclosed in U.S. Plant Pat. No. No. 30,430. In side-by-side comparisons plants of the new *Abelia* differ from plants of 'Minacara1' in the following characteristics:

1. Plants of the new *Abelia* are more mounding than plants of 'Minacara1'.
2. Plants of the new *Abelia* have smaller flowers than plants of 'Minacara1'.

3. Plants of the new *Abelia* and 'Minacara1' differ in flower color as flowers of plants of 'Minacara1' have lavender purple-colored flowers.

BRIEF DESCRIPTION OF THE PHOTOGRAPHS

The accompanying colored photographs illustrate the overall appearance of the new *Abelia* plant showing the colors as true as it is reasonably possible to obtain in colored reproductions of this type. Colors in the photographs may differ slightly from the color values cited in the detailed botanical description which accurately describe the colors of the new *Abelia* plant.

The photograph on the first sheet is a side perspective view of a typical plant of 'RNTOM' grown in a container.

The photograph on the second sheet is a close-up view of a typical plant of 'RNTOM'.

DETAILED BOTANICAL DESCRIPTION

The aforementioned photographs and following observations, measurements and values describe plants grown during the late spring and summer in three-gallon containers in outdoor nurseries in Park Hill, Okla. and Fort Worth, Tex. and under cultural practices typical of commercial *Abelia* production. During the production of the plants, day temperatures ranged from −5° C. to 40° C. and night temperatures ranged from −20° C. to 35° C. Plants were three years old when the photographs were taken and four years old when the description was taken. In the description, color references are made to The Royal Horticultural Society Colour Chart, 2007 Edition, except where general terms of ordinary dictionary significance are used.

Botanical classification: *Abelia* x *grandiflora* 'RNTOM'.

Parentage: Naturally-occurring branch mutation of *Abelia* x *grandiflora* 'Canyon Creek', not patented.

Propagation:

- *Type*.—By semi-hardwood and hardwood cuttings.
- *Time to initiate roots, summer*.—About 35 to 50 days at ambient temperatures about 27° C. to 30° C.
- *Time to initiate roots, winter*.—About 45 to 70 days at ambient temperatures about 16° C. to 17° C.
- *Time to produce a rooted young plant, summer*.—About 65 to 90 days at ambient temperatures about 27° C. to 30° C.
- *Time to produce a rooted young plant, winter*.—About 90 to 120 days at ambient temperatures about 16° C. to 17° C.
- *Root description*.—Thin to medium in thickness, fibrous; typically white to light brown in color, actual color of the roots is dependent on substrate composition, water quality, fertilizer type and formulation, substrate temperature and physiological age of roots.
- *Rooting habit*.—Freely branching; medium density to dense.

Plant description:

- *Plant form and growth habit*.—Perennial shrub; compact, uniformly upright to somewhat outwardly spreading and rounded plant habit; low to moderately vigorous growth habit.
- *Branching habit*.—Freely branching habit, dense and bushy growth habit with about twelve primary lateral branches per plant with secondary lateral branches potentially developing at every node; pinching enhances lateral branch development.
- *Plant height*.—About 31 cm.
- *Plant diameter* (*area of spread*).—About 43 cm.

Lateral branch description:

- *Length*.—About 27.5 cm.
- *Diameter*.—About 3.5 mm.
- *Internode length*.—About 1.3 cm.
- *Aspect*.—Upright to outwardly.
- *Texture and luster, developing*.—Smooth, glabrous; matte.
- *Texture and luster, fully developed*.—Woody; matte.
- *Color, developing*.—Upper surface, close to 178A to 178B; lower surface, close to 144B to 144C.
- *Color, fully developed*.—Close to 197D.

Leaf description:

- *Arrangement*.—Opposite, simple.
- *Length*.—About 3.1 cm.
- *Width*.—About 1.6 cm.
- *Shape*.—Ovate.
- *Apex*.—Acuminate.
- *Base*.—Obtuse.
- *Margin*.—Crenate.
- *Texture and luster, upper surface*.—Smooth, glabrous; glossy.
- *Texture and luster, lower surface*.—Smooth, glabrous; slightly glossy.
- *Venation pattern*.—Pinnate.
- *Color, full sunlight conditions*.—Developing leaves, upper surface: Close to 9A tinged with close to 15A. Developing leaves, lower surface: Close to 9B to 9C slightly tinged with close to 15A. Fully expanded leaves, upper surface: Close to between N144A and 144A; venation, close to between N144A and 144A. Fully expanded leaves, lower surface: Slightly lighter green than 144A; venation, slightly lighter green than 144A.
- *Color, shade conditions*.—Developing leaves, upper surface: Close to between N144A and 144A. Developing leaves, lower surface: Close to 144A to 144B. Fully expanded leaves, upper surface: Close to 147A; venation, close to 147A. Fully expanded leaves, lower surface: Close to 147B; venation, close to 147B.
- *Petioles*.—Length: About 3.5 mm. Diameter: About 1.5 mm. Texture and luster, upper and lower surfaces: Smooth, glabrous; matte. Color, upper surface: Close to 144A. Color, lower surface: Close to 144A to 144B.

Flower description:

- *Flower appearance and arrangement*.—Single funnel-form flowers arranged on terminal panicles; freely flowering habit with about six flowers per inflorescence and about 35 to 40 flowers developing per plant; flower face upright to outwardly.
- *Inflorescence height*.—About 2.8 cm.
- *Inflorescence width*.—About 5 cm.
- *Fragrance*.—Slightly fragrant; pleasant.
- *Natural flowering season*.—Plants begin flowering in early summer and flower until frost in Oklahoma; flowers not persistent.
- *Flower diameter*.—About 1.5 cm.
- *Flower depth*.—About 1.7 cm.
- *Flower buds*.—Length: About 1.9 cm. Diameter: Towards the apex, about 5 mm; towards the base, about 1 mm. Shape: Lanceolate to spatulate. Color: Towards the apex, close to 57A; towards the base, close to 1C.

*Petals*.—Quantity and arrangement: Five fused petals arranged in a single whorl; petals slightly recurved. Lobe length: About 7 mm. Lobe width: About 5 mm. Shape: Elliptic to obovate. Apex: Obtuse; slightly recurved. Base: Obtuse, fused. Margin: Entire. Texture, upper and lower surfaces: Smooth, glabrous; thick and fleshy. Color: When opening, upper and lower surfaces: Close to 155D. Fully opened, upper and lower surfaces: Close to 155D.

*Sepals*.—Quantity and arrangement: Five fused sepals arranged in a single whorl. Length: About 9 mm. Width: About 3 mm. Shape: Lanceolate to oblanceolate. Apex: Acute. Base: Cuneate. Margin: Entire. Texture, upper and lower surfaces: Smooth, glabrous; along the margins, pubescent. Color, upper surface: Close to 182A. Color, lower surface: Close to 146D.

*Peduncles*.—Length: About 5 cm. Diameter: About 1 mm. Strength: Strong. Texture: Pubescent. Angle: Upright to outwardly. Color: Close to 144B.

*Pedicels*.—Length: About 5 mm. Diameter: About 2 mm. Strength: Strong. Texture: Pubescent. Angle: Upright to outwardly. Color: Close to 144B.

*Reproductive organs*.—Stamens: Quantity per flower: Five. Filament length: About 1 mm. Filament color: Close to 155D. Anther length: About 1 mm. Anther shape: Oblong. Anther color: Close to 155C. Pollen amount: Scarce. Pollen color: Close to 155C. Pistils: Quantity per flower: One. Pistil length: About 1.5 cm. Stigma shape: Globular. Stigma color: Close to 134A. Style length: About 1.5 cm. Style color: Close to 155C. Ovary color: Close to 144B Seeds and fruits: To date, seed and fruit production have not been observed on plants of the new *Abelia*.

Garden performance: Plants of the new *Abelia* have been observed to have good garden performance and to tolerate rain, wind and temperatures ranging from about −23C to about 42C.

Pathogen & pest resistance: To date, plants of the new *Abelia* have not been shown to be resistant to pathogens and pests common to *Abelia* plants.

It is claimed:

1. A new and distinct *Abelia* plant named 'RNTOM' as illustrated and described.

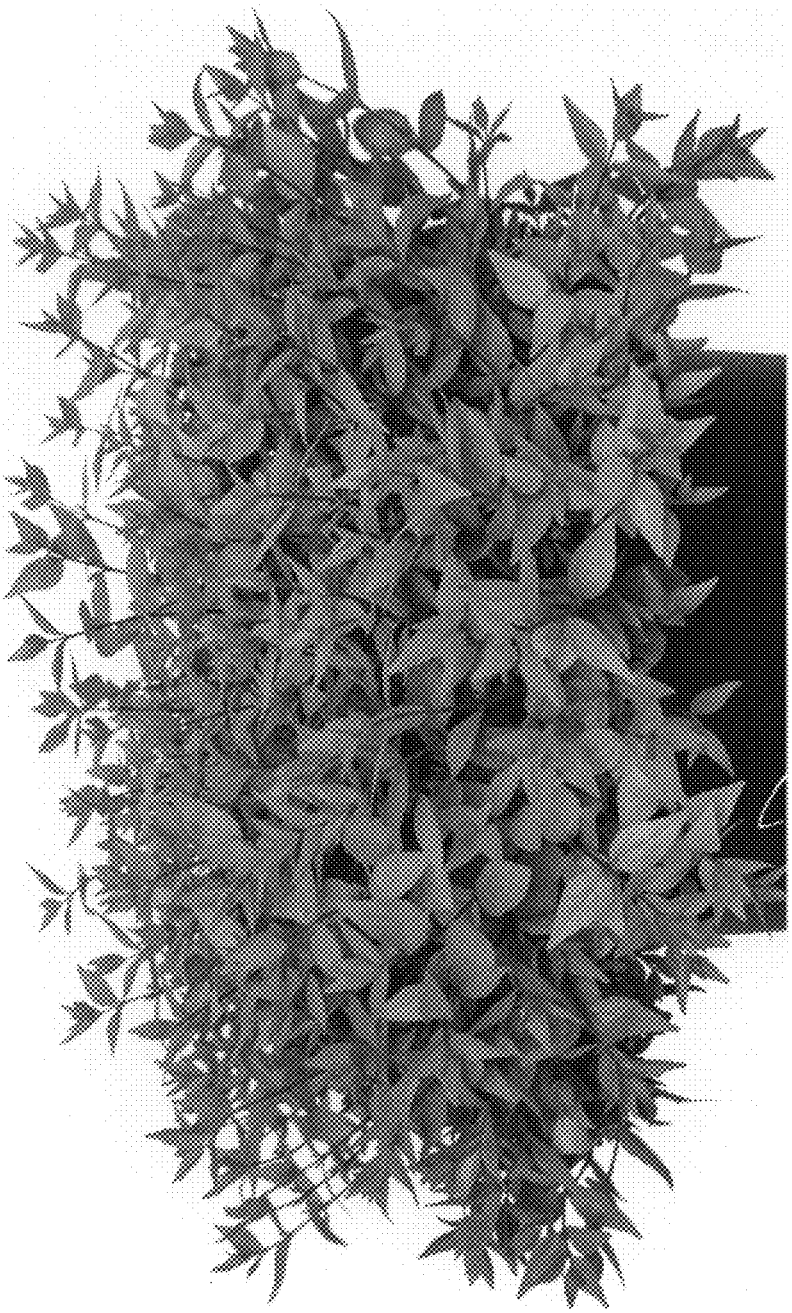

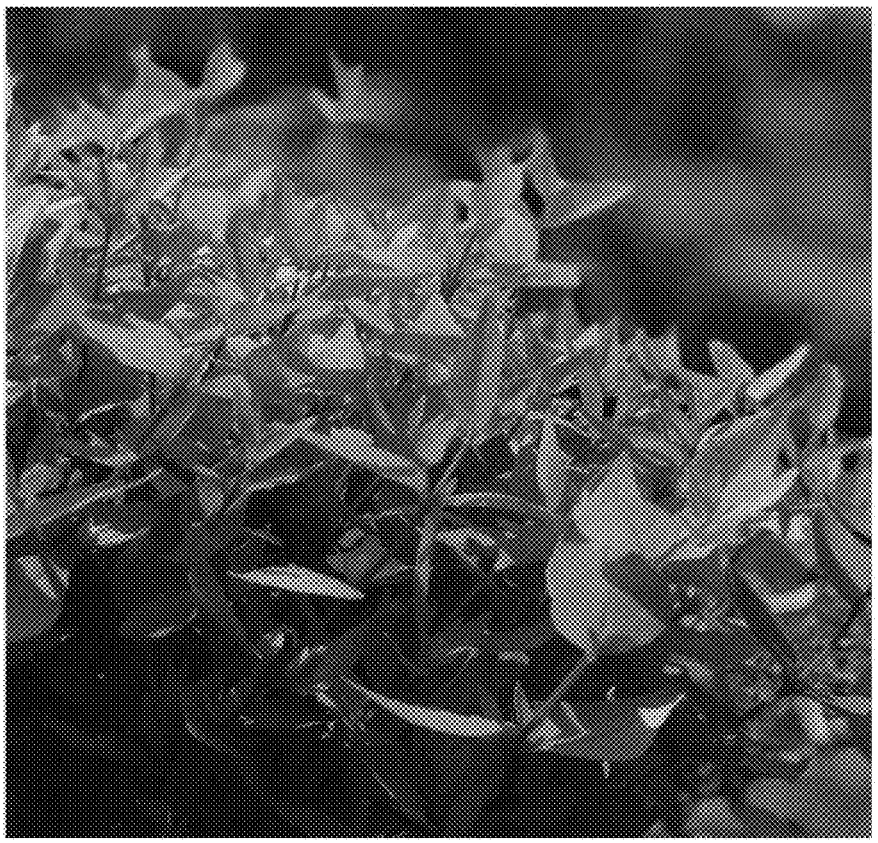

* * * * *